United States Patent
Syed

(10) Patent No.: US 9,980,838 B2
(45) Date of Patent: May 29, 2018

(54) APPARATUS AND METHOD FOR A BIFURCATED CATHETER FOR USE IN HOSTILE AORTIC ARCHES

(71) Applicant: RAM Medical, LLC, Springfield, OH (US)

(72) Inventor: Mubin I. Syed, Springfield, OH (US)

(73) Assignee: RAM MEDICAL INNOVATIONS LLC, Springfield, OH (US)

(*) Notice: Subject to any disclaimer, the term of this patent is extended or adjusted under 35 U.S.C. 154(b) by 16 days.

(21) Appl. No.: 14/929,030

(22) Filed: Oct. 30, 2015

(65) Prior Publication Data

US 2017/0119562 A1     May 4, 2017

(51) Int. Cl.
| | | |
|---|---|---|
| A61F 2/95 | (2013.01) | |
| A61F 2/954 | (2013.01) | |
| A61F 2/962 | (2013.01) | |

(52) U.S. Cl.
CPC .............. *A61F 2/954* (2013.01); *A61F 2/962* (2013.01)

(58) Field of Classification Search
CPC .. A61F 2/954; A61F 2/962; A61F 2/95; A61F 2/958; A61F 2017/1205; A61F 2002/9517; A61F 2/02; A61F 2/04; A61B 17/12022; A61B 17/32056; A61B 2002/9517; A61B 17/12118
USPC ........................................................ 606/108
See application file for complete search history.

(56) References Cited

U.S. PATENT DOCUMENTS

| | | |
|---|---|---|
| 4,243,040 A | 1/1981 | Beecher |
| 5,098,707 A | 3/1992 | Baldwin et al. |
| 5,293,772 A | 9/1994 | Carr, Jr. |
| 5,344,426 A | 9/1994 | Lau et al. |
| 5,419,777 A | 5/1995 | Hofling |

(Continued)

FOREIGN PATENT DOCUMENTS

| | | |
|---|---|---|
| EP | 3280355 A1 | 2/2018 |
| WO | 1996036269 | 11/1996 |

(Continued)

OTHER PUBLICATIONS

John, Godwin, Z0250 Lab III Sep. 16, 2002 https://projects.ncsu.edu/cals/course/zo250/lab-3.html.*

(Continued)

*Primary Examiner* — Victor Nguyen

(74) *Attorney, Agent, or Firm* — Jennifer Hayes; Nixon Peabody LLP

(57) ABSTRACT

Systems and methods for addressing the percutaneous intervention related trauma to the vessels that arise from type-III hostile aortic arches, from uncontrolled prolapse of sheaths, embolic protection devices and stent delivery systems, by stabilizing the systems while stenting of the left and right carotid arteries. Guide wires to stabilize catheters used to access the left or right carotid arteries (CA) for carotid percutaneous intervention of the vessels originating from a tortuous aortic arch are disclosed. A bifurcated catheter for stabilizing the catheters is also disclosed. The bifurcated catheter has a main catheter that divides into two separate catheters forming a "Y" shape. One leg of the catheter has a smaller diameter with a smaller working lumen (inner diameter) to carry the stabilizing wire and the other leg of the catheter has a larger working lumen for arterial stenting operations.

24 Claims, 12 Drawing Sheets

Cross section of the bifurcated catheter within the sheath catheter close to the point of bifurcation (Not to scale)

(56) References Cited

U.S. PATENT DOCUMENTS

| | | |
|---|---|---|
| 5,571,135 A | 11/1996 | Fraser et al. |
| 5,651,366 A | 7/1997 | Liang et al. |
| 5,662,703 A | 9/1997 | Yurek et al. |
| 5,669,924 A | 9/1997 | Shaknovich |
| 5,690,644 A | 11/1997 | Yurek et al. |
| 5,718,702 A | 2/1998 | Edwards |
| 5,720,735 A | 2/1998 | Dorros |
| 5,807,330 A | 9/1998 | Teitelbaum |
| 5,957,901 A | 9/1999 | Mottola et al. |
| 6,027,462 A | 2/2000 | Greene et al. |
| 6,059,813 A | 5/2000 | Vrba et al. |
| 6,152,141 A | 11/2000 | Stevens et al. |
| 6,238,410 B1 | 5/2001 | Vrba et al. |
| 6,544,278 B1 | 4/2003 | Vrba et al. |
| 6,663,613 B1 | 12/2003 | Lewis et al. |
| 6,780,174 B2 | 8/2004 | Mauch |
| 6,808,520 B1 | 10/2004 | Fouirkas et al. |
| 6,837,881 B1 | 1/2005 | Barbut |
| 6,929,633 B2 | 8/2005 | Evans et al. |
| 6,942,682 B2 | 9/2005 | Vrba et al. |
| 7,393,358 B2 | 7/2008 | Malewicz |
| 7,758,624 B2 | 7/2010 | Dorn et al. |
| 7,763,010 B2 | 7/2010 | Evans et al. |
| 7,766,961 B2 | 8/2010 | Patel et al. |
| 7,842,026 B2 | 11/2010 | Cahill et al. |
| 7,955,370 B2 | 6/2011 | Gunderson |
| 8,092,509 B2 | 1/2012 | Dorn et al. |
| 8,202,309 B2 | 6/2012 | Styrc |
| 8,241,241 B2 | 8/2012 | Evans et al. |
| 8,343,181 B2 | 1/2013 | Duffy et al. |
| 8,535,290 B2 | 9/2013 | Evans et al. |
| 8,721,714 B2 | 5/2014 | Kelley |
| 8,727,988 B2 | 5/2014 | Flaherty et al. |
| 8,740,971 B2 | 6/2014 | Iannelli |
| 8,986,241 B2 | 3/2015 | Evans et al. |
| 8,998,894 B2 | 4/2015 | Mauch et al. |
| 9,314,499 B2 | 4/2016 | Wang et al. |
| 9,636,244 B2 | 5/2017 | Syed |
| 2001/0003985 A1 | 6/2001 | Lafontaine et al. |
| 2001/0049534 A1 | 12/2001 | Lachat |
| 2002/0077691 A1 | 6/2002 | Nachtigall |
| 2002/0123698 A1 | 9/2002 | Garibotto et al. |
| 2002/0156518 A1 | 10/2002 | Tehrani |
| 2003/0088187 A1 | 5/2003 | Saadat et al. |
| 2004/0073190 A1 | 4/2004 | Deem et al. |
| 2004/0147837 A1 | 7/2004 | MacAulay et al. |
| 2005/0043779 A1 | 2/2005 | Wilson |
| 2005/0101968 A1 | 5/2005 | Dadourian |
| 2005/0113862 A1 | 5/2005 | Besselink et al. |
| 2005/0222488 A1 | 10/2005 | Chang et al. |
| 2006/0025752 A1 | 2/2006 | Broaddus et al. |
| 2006/0025844 A1 | 2/2006 | Majercak et al. |
| 2006/0030923 A1 | 2/2006 | Gunderson |
| 2006/0155363 A1* | 7/2006 | LaDuca .............. A61F 2/856 623/1.16 |
| 2006/0200221 A1 | 9/2006 | Malewicz |
| 2006/0257389 A1 | 11/2006 | Binford |
| 2006/0259063 A1 | 11/2006 | Bates et al. |
| 2006/0270900 A1 | 11/2006 | Chin et al. |
| 2007/0038061 A1 | 2/2007 | Huennekens et al. |
| 2007/0038293 A1 | 2/2007 | St. Goar et al. |
| 2007/0049867 A1 | 3/2007 | Shindelman |
| 2007/0118151 A1 | 5/2007 | Davidson et al. |
| 2007/0129719 A1 | 6/2007 | Kendale et al. |
| 2008/0039746 A1 | 2/2008 | Hissong et al. |
| 2008/0114239 A1 | 5/2008 | Randall et al. |
| 2008/0194993 A1 | 8/2008 | McLaren et al. |
| 2008/0208309 A1* | 8/2008 | Saeed .............. A61F 2/07 623/1.11 |
| 2008/0281398 A1 | 11/2008 | Koss |
| 2009/0005679 A1 | 1/2009 | Dala-Krishna |
| 2009/0132019 A1* | 5/2009 | Duffy .............. A61F 2/954 623/1.11 |
| 2009/0171293 A1 | 7/2009 | Yang et al. |
| 2009/0177035 A1 | 7/2009 | Chin |
| 2009/0254116 A1 | 10/2009 | Rosenschein et al. |
| 2009/0270975 A1 | 10/2009 | Giofford, III et al. |
| 2009/0319017 A1 | 12/2009 | Berez et al. |
| 2010/0024818 A1 | 2/2010 | Stenzler et al. |
| 2010/0030165 A1 | 2/2010 | Takagi et al. |
| 2010/0030256 A1 | 2/2010 | Dubrul et al. |
| 2010/0069852 A1 | 3/2010 | Kelley |
| 2010/0168583 A1 | 7/2010 | Dausch et al. |
| 2010/0185161 A1 | 7/2010 | Pellegrino et al. |
| 2010/0185231 A1 | 7/2010 | Lashinski |
| 2010/0204708 A1 | 8/2010 | Sharma |
| 2010/0268067 A1 | 10/2010 | Razzaque et al. |
| 2010/0272740 A1 | 10/2010 | Vertegel et al. |
| 2011/0009943 A1 | 1/2011 | Paul et al. |
| 2011/0034987 A1 | 2/2011 | Kennedy |
| 2011/0071394 A1 | 3/2011 | Fedinec |
| 2011/0082533 A1 | 4/2011 | Vardi et al. |
| 2011/0224773 A1 | 9/2011 | Gifford et al. |
| 2011/0230830 A1 | 9/2011 | Gifford, III et al. |
| 2011/0270375 A1 | 11/2011 | Hartley et al. |
| 2012/0016343 A1 | 1/2012 | Gill |
| 2012/0020942 A1 | 1/2012 | Hall et al. |
| 2012/0022636 A1 | 1/2012 | Chobotov |
| 2012/0034205 A1 | 2/2012 | Alkon |
| 2012/0035590 A1 | 2/2012 | Whiting et al. |
| 2012/0169712 A1 | 7/2012 | Hill et al. |
| 2012/0209375 A1 | 8/2012 | Madrid et al. |
| 2012/0289945 A1 | 11/2012 | Segermark |
| 2013/0053792 A1 | 2/2013 | Fischell et al. |
| 2013/0131777 A1 | 5/2013 | Hartley et al. |
| 2013/0296773 A1 | 11/2013 | Feng et al. |
| 2013/0331819 A1 | 12/2013 | Rosenman et al. |
| 2013/0331921 A1 | 12/2013 | Roubin |
| 2014/0031925 A1 | 1/2014 | Garrison et al. |
| 2014/0142427 A1 | 5/2014 | Petroff |
| 2014/0214002 A1 | 7/2014 | Lieber et al. |
| 2014/0228808 A1* | 8/2014 | Webster .............. A61M 25/0041 604/510 |
| 2015/0018942 A1 | 1/2015 | Hung et al. |
| 2015/0174377 A1 | 6/2015 | Syed |
| 2015/0190576 A1 | 7/2015 | Lee et al. |
| 2015/0201900 A1 | 7/2015 | Syed |
| 2015/0245933 A1 | 9/2015 | Syed |
| 2015/0352331 A1 | 12/2015 | Helm, Jr. |
| 2015/0366536 A1 | 12/2015 | Courtney et al. |
| 2015/0374261 A1 | 12/2015 | Grunwald |
| 2016/0008058 A1 | 1/2016 | Hu et al. |
| 2016/0038724 A1 | 2/2016 | Madsen et al. |
| 2016/0120509 A1 | 5/2016 | Syed |
| 2016/0120673 A1* | 5/2016 | Siegel .............. A61B 17/12109 623/1.23 |
| 2016/0296355 A1 | 10/2016 | Syed |
| 2016/0338835 A1 | 11/2016 | Van Bladel et al. |
| 2017/0119563 A1 | 5/2017 | Syed |
| 2017/0135833 A1 | 5/2017 | Syed |
| 2017/0181876 A1 | 6/2017 | Syed |
| 2017/0304095 A1 | 10/2017 | Syed |
| 2017/0361062 A1 | 12/2017 | Syed |
| 2018/0042743 A1 | 2/2018 | Syed |
| 2018/0059124 A1 | 3/2018 | Syed |

FOREIGN PATENT DOCUMENTS

| | | |
|---|---|---|
| WO | 2011/106502 | 9/2011 |
| WO | 2010/129193 A1 | 11/2011 |
| WO | 2012030101 | 8/2012 |
| WO | 2014081947 | 5/2014 |
| WO | 2014197839 | 12/2014 |
| WO | 2016164215 | 10/2016 |
| WO | 2017127127 A1 | 7/2017 |
| WO | 2017222571 A1 | 12/2017 |
| WO | 2017222612 A1 | 12/2017 |

OTHER PUBLICATIONS

International Search Report and Written Opinion issued for International Application No. PCT/US2016/047165 dated Jan. 5, 2017, 13 pages.

(56) References Cited

OTHER PUBLICATIONS

Stroke Treatments, American Heart Association, Retrieved from: Http://www.strokeassociation.org/STROKEORG/AboutStroke/Treatment/Stroke-Treatments_UCM_310892_Article_jsp#V9Hrg2WfV_1.

Beckman et al., Venous Thromboembolism: A Public Health Concern, Am J Prev Med., 2010, vol. 38(4), pp. S495-S501.

Meunier et al., Individual Lytic Efficacy of Recombinant Tissue Plasminogen Activator in an in-vitro Human Clot Model: Rate of Nonresponse Acad Emerg Med., 2013, vol. 20(5), pp. 449-455.

Tripathi et al., Use of Tissue Plasminogen Activator for Rapoid Dissolution of Fibrin and Blood Clots in the Eye After Surgery for Claucomoa and Cataract in Humans, Drug Development Research, 1992, vol. 27(2), pp. 147-159.

International Search Report and Written Opinion for International Application No. PCT/US2016/024795 dated Aug. 30, 2016, 14 pages.

International Search Report and Written Opinion issued for International Application No. PCT/US2016/024794 dated Jul. 1, 2016, 10 pages.

International Search Report and Written Opinion issued for International Application No. PCT/US2016/047163 dated Oct. 28, 2016, 9 pages.

Supplemental Response to Office Action in U.S. Appl. No. 13/750,920 dated Nov. 2, 2015.

Office Action in U.S. Appl. No. 13/750,920 dated Nov. 5, 2015.

Response to Office Action in U.S. Appl. No. 13/750,920 dated Feb. 11, 2016.

International Search Report and Written Opinion issued for International Application No. PCT/US2017/021188 dated May 10, 2017, 11 pages.

International Search Report issued in International Application No. PCT/US2013/071271 dated Feb. 10, 2014, 2 pages.

Written Opinion issued in International Application No. PCT/US2013/071271 dated Feb. 10, 2014, 5 pages.

International Preliminary Report on Patentability issued in International Application No. PCT/US2013/071271 dated May 26, 2014, 6 pages.

Office Action issued in U.S. Appl. No. 13/750,920 dated Apr. 8, 2015.

Response to Office Action in U.S. Appl. No. 13/750,920 dated Aug. 10, 2015.

International Search Report and Written Opinion issued for PCT/US2018/012834 dated Mar. 15, 2018, 13 pages.

\* cited by examiner

Cross section of the bifurcated catheter within the sheath catheter close to the point of bifurcation ( Not to scale)

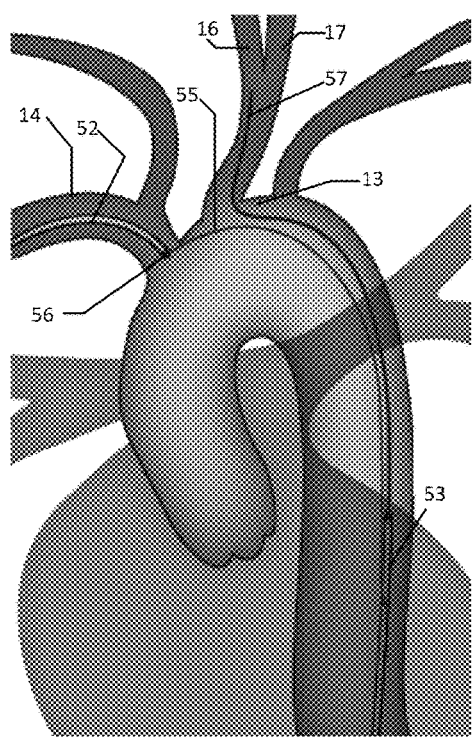 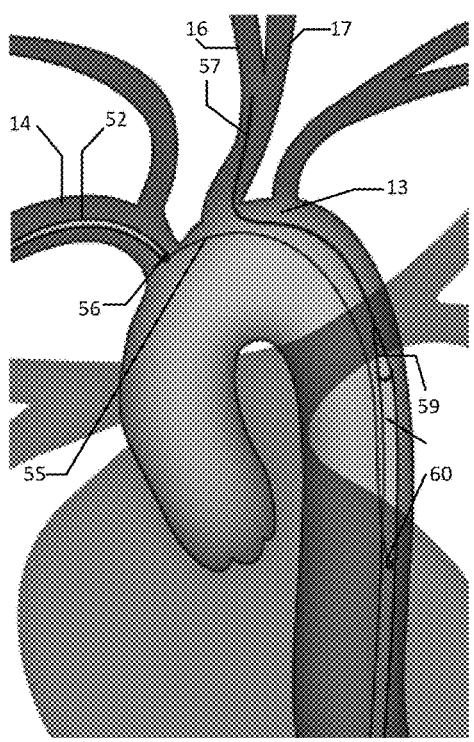
Figure 13                              Figure 14

APPARATUS AND METHOD FOR A BIFURCATED CATHETER FOR USE IN HOSTILE AORTIC ARCHES

BACKGROUND

1. Field

The invention relates to improved methods and apparatus used in catheter based interventional procedures, mainly involving type II and III hostile aortic arches, and the access and deployment of stents in the carotid arteries and procedures above the neck.

2. Related Art

Stenting of the carotid artery (CA) is relatively new to interventional procedures. It is a challenging procedure because accessing the left or right carotid artery can be dependent on the anatomical disposition of the aortic arch.

FIG. 1 illustrates the aortic arch. As shown in FIG. 1, the a aorta 1 includes an aortic arch region 3, a descending aorta 2, and an innominate 4. Three types of arches shown in FIG. 1: Type I, Type II and Type III arches. Also shown in FIG. 1 is the right subclavian artery (RSA) 5, left subclavian artery (LSA) 6, right common carotid artery (RCCA) 7 and left common carotid artery (LCCA) 8.

The arch types are defined by the height of the top of the aortic arch 3 from the base location where the innominate 4 attaches to the aorta. In a type I arch, the height is less than the diameter of the common carotid artery (CCA). Similarly, in a type II arch, the height of the top of the arch 3 from the base of the innominate 4 is of the order of 1 to 2 times the diameter of the CCA. In a type III arch, the height is more than twice the diameter of the CCA. As the height of the arch increases the procedures within the carotid arteries become more and more difficult due to the tortuous nature of the arterial connections to the aorta at the arch.

In type III hostile aortic arches, the arch itself can be very acute thus making the access of the left or right carotid arteries ostium difficult. Subsequent placement of a stent delivery system in a stable mode into the arterial system above it therefore becomes more difficult. The stenting procedure itself is meant to re-establish a more normalized blood flow through the carotid and internal carotid artery into the brain by opening up regions of the artery constricted by plaque deposits which inhibit flow. The stents themselves can be self-expanding, balloon expandable, bio-absorbable, and/or covered. The stent delivery systems are designed to accommodate very acute bends but are reliant upon the guide catheter and guide wires and or embolic protection devices to stabilize them during deployment. Stents have been used to open "stenosis"—semi-occluded sections of the arterial system—for many years. They come in a wide variety and are designed for specific areas of the body, these include: balloon expandable, self-expanding, covered and bio-absorbable stents. Stenting in the neck and procedures above the neck are challenging when confronted with a type III hostile aorta, in particular stenting of the left or right carotid artery. During the insertion, manipulation and stabilization of the stent delivery mechanism and during removal of the guide wire and secondary wire, injuries to the subclavian artery and the tortuous aortic arch can happen. This can be caused by uncontrolled collapse of the sheath, embolic protection device (EPD) and stent/stent delivery system in the ascending aorta during procedure. This type of prolapse can result in the patient suffering cerebral embolism or stroke by dragging the fully deployed EPD over the carotid stenosis. Further, dragging the guide wires over the tortuous arterial regions can cause cutting into the arterial walls or otherwise injuring the artery resulting in dissections and trauma to the vessels involved. These traumas can be dangerous to the patient as they can ultimately directly affect blood flow by leakage at the dissections or by creating accumulation of thrombus, an organization of blood cells, which is a natural reaction to vessel injury. These may require additional procedures to repair and heal the damaged artery walls and prevent problems.

Accordingly, what is needed is systems and methods to stabilize the sheath, the EPD and the stent delivery system within the carotid arterial system to reduce the injuries caused to the arterial walls during stenting and other minimally invasive treatment of the carotid arteries and above the neck procedures.

SUMMARY

The following summary of the invention is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

In accordance with one aspect of the invention, a carotid percutaneous intervention system is disclosed that includes a sheath catheter percutaneously insertable and positionable in an aortic arch; a guidewire deliverable through percutaneous femoral artery access; and a stabilization wire comprising a snare slideably inserted through the sheath catheter, the stabilization wire configured to snare the guidewire and pull a portion of the guidewire within the sheath catheter.

The system may further include a reverse curve catheter insertable through the sheath catheter parallel to the stabilization wire.

The system may further include a stiff guidewire insertable through the reverse curve catheter.

The system may further include a bifurcated catheter inserted through the sheath catheter over the stabilization wire.

The bifurcation catheter may include a common catheter portion at a proximal end of the bifurcation catheter; a first leg at a distal end of the bifurcation catheter, wherein the first leg is deliverable over the stiff wire to a treatment site; and a second leg at a distal end of the bifurcation catheter, wherein the second leg is positionable over the stabilization wire, wherein the first leg and the second leg join with the common catheter portion at a junction. The junction may be Y-shaped.

The bifurcated catheter may be pre-loaded into the sheath catheter.

The bifurcated catheter may include a procedural lumen and a stabilization lumen. The procedural lumen may extend from the proximal end through the common catheter to the distal end through the first leg, and the stabilization lumen may extend from the proximal end through the common catheter to the distal end through the second leg. The stabilization lumen may be for slideably receiving a snare catheter and the stabilization wire.

A distal tip of the first leg and a distal tip of the second leg may include atraumatic tips.

The system may further include a procedural catheter insertable through the first leg of the bifurcated catheter.

The stabilization wire may be further configured to snare the guidewire and pull a portion of the guidewire within the bifurcated catheter.

The stabilization wire may be configured to pull the guide wire through a proximal end of the sheath.

Tension may be applicable to the ensnared guidewire and stabilization wire to stabilize the system.

In accordance with another aspect of the invention, a carotid percutaneous intervention system is disclosed that includes a sheath catheter percutaneously insertable and positionable in an aortic arch; a wire comprising a snare slideably inserted the sheath catheter; a reverse curve catheter advanceable into an innominate, the reverse curve catheter comprising a proximal end and a distal end and including a hole near the distal end; a stabilization wire extendable from the hole of the reverse curve catheter at the aortic arch, wherein the wire comprising the snare is configured to snare the stabilization wire and pull a portion of the stabilization wire within the sheath catheter.

The system may further include a stiff guidewire insertable through the reverse curve catheter and at the treatment site in the carotid artery.

The reverse curve catheter may be removable following delivery of the stiff guidewire in the carotid artery.

The system may further include a bifurcated catheter insertable over the stabilization wire and the stiff guidewire into the carotid artery.

The bifurcation catheter may include a common catheter portion at a proximal end of the bifurcation catheter; a first leg at a distal end of the bifurcation catheter, wherein the first leg is deliverable over the stiff wire to a treatment site; and a second leg at a distal end of the bifurcation catheter, wherein the second leg is positionable over the stabilization wire, wherein the first leg and the second leg join with the common catheter portion at a junction. The junction may be Y-shaped.

The bifurcated catheter may include a procedural lumen and a stabilization lumen.

The system may further include a procedural catheter insertable through the bifurcated catheter after removal of the stiff guidewire.

In accordance with yet another aspect of the invention, a bifurcated catheter for use in a carotid percutaneous intervention system is disclosed that includes a body comprising a proximal end and a distal end, wherein the body includes a common catheter portion at the proximal end; a first leg at the distal end; and a second leg at a distal end, wherein the first leg and the second leg join with the common catheter portion at a junction.

The junction may be Y-shaped.

The body may include a procedural lumen and a stabilization lumen that extend from the proximal end to the distal end of the body.

The procedural lumen may extend from the proximal end through the common catheter to the distal end through the first leg, and the stabilization lumen may extend from the proximal end through the common catheter to the distal end through the second leg.

The stabilization lumen may be for slideably receiving a stabilization wire.

A distal tip of the first leg and a distal tip of the second leg may include atraumatic tips.

The bifurcated catheter may reduce trauma to the vessels while providing stabilization to a process catheter for procedures within a carotid arterial system.

The bifurcated catheter may protect a right innominate, carotid artery and subclavian artery of a patient during manipulation of a guide wire.

In accordance with a further aspect of the invention, a method for carotid percutaneous intervention is disclosed that includes advancing a guidewire to the aortic arch using radiographic imaging; advancing a sheath catheter over the guidewire to the descending aorta; advancing a snare wire to the aortic arch; ensnaring the guidewire with the snare wire to form a stabilization wire and pulling the stabilization wire into the sheath catheter.

The snare wire may be advanced out of a small leg of a bifurcated catheter and the snare wire may pull the stabilization wire through the bifurcated catheter.

The guidewire may be pulled through a proximal end of the bifurcated catheter.

The method may further include inserting the guidewire through percutaneous femoral artery access.

The method may further include advancing a reverse guide catheter and second guidewire up an operational lumen of the bifurcated catheter into a common carotid artery, wherein the second guidewire is stiffer than the guidewire.

The method may further include removing the reverse guide wire after delivering the second guidewire.

The method may further include advancing the bifurcated catheter such that the operational lumen of the bifurcated catheter advances over the second guidewire to a treatment site.

The method may further include removing the second guidewire and performing a treatment operation at the treatment site.

The method may further include advancing a reverse curve catheter into the descending aorta, and wherein the guidewire extends through a hole near a distal end of the reverse curve catheter.

The method may further include delivering a second guidewire into the carotid artery and removing the reverse curve catheter.

The method may further include delivering a bifurcated catheter to a treatment site.

The bifurcated catheter may include a stabilization lumen and an operational lumen, and wherein delivering the bifurcated catheter to the treatment site may include advancing the stabilization lumen over the stabilization wire and advancing the operational lumen over the second guidewire.

The method may further include removing the second guidewire and performing a treatment operation at the treatment site.

The method may further include applying tension to the stabilization wire.

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments.

FIG. 6A is a cross-sectional view of a portion of the bifurcated catheter in accordance with one embodiment of the invention.

FIG. 13 is a schematic diagram showing the removal of the reverse catheter leaving the guide wire and the stabilization wire in place in accordance with one embodiment of the invention.

FIG. 14 is a schematic diagram of the working sheath catheter, having an atraumatic tip and the working sheath catheter having a second chamber for the guide wire extending out of a side hole, being advanced over the guide wire in accordance with one embodiment of the invention.

DETAILED DESCRIPTION

Figure 1:
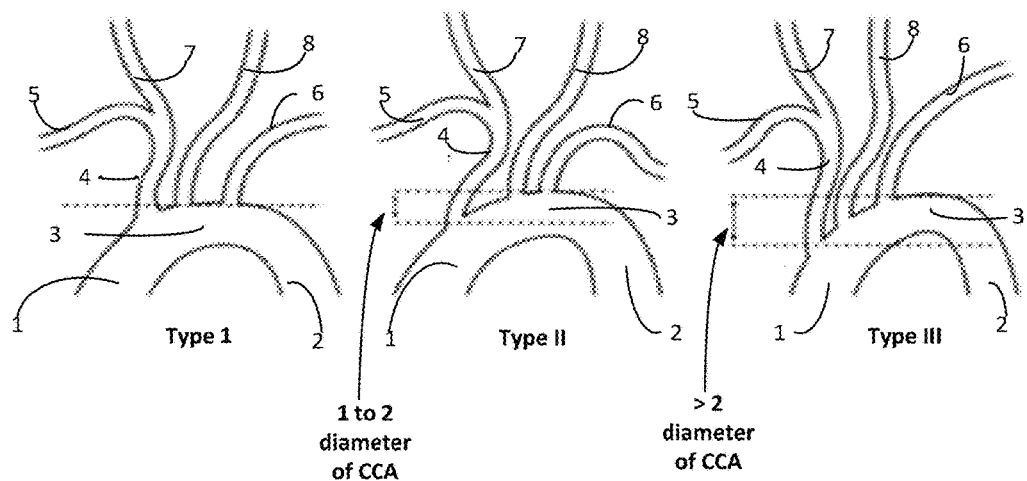
FIG. 1 is a schematic diagram illustrate the three types of aortic arches encountered in humans.

Embodiments of the invention are directed to new devices and associated methods for the placement of stents in the carotid artery, and especially into the left or right carotid arteries, for procedures above the neck. These new devices and associated methods stabilize the working lumen or delivery sheath for the carotid stent delivery system. These new devices and associated methods also protect the innominate and subclavian artery as well as the aortic arch from trauma during stenting and other procedures above the neck where there is a possibility for trauma to the arteries as a result of tension on the secondary or stabilization guidewire. This is especially true in the case of patients with type II and Type III aortic arch.

Embodiments of the invention are directed to the application and use of guide wires for stabilization of the catheters used to access the left or right carotid arteries (CA) for carotid percutaneous intervention of the vessels originating from a tortuous aortic arch.

Embodiments of the invention use a bifurcated catheter having a main catheter arm that is used to extend into the region of the procedure and a support catheter arm that extends into the right subclavian artery to provide protection to that vessel during tightening of a support and stabilization wire through the right subclavian artery. The head of a sheath/guide catheter is at that time placed in the aorta, at the branching of either innominate or the left or right carotid artery through which the procedural arm of the bifurcated catheter, that is the second branch of the bifurcated catheter, has to be extended to conduct the procedure or place the stent. The correct placement of the head of the sheath catheter and the extension of the support catheter to cover the support wire enable the wires to be extended and retracted without damage to the arch and the arterial vessels used during procedure.

In some embodiments, the bifurcated catheter includes a main catheter that divides into two separate catheters forming a "Y" shape. One leg of the bifurcated catheter has a smaller diameter with a smaller working lumen (inner diameter) to carry the stabilizing wire and the second leg of the bifurcated catheter has a larger working lumen for arterial stenting operations/procedures. This bifurcated catheter addresses the percutaneous intervention related trauma to the vessels that arise from type-II or type-III hostile aortic arches, from uncontrolled prolapse of the sheath, embolic protection device and stent delivery system, by stabilizing the systems, using a through-and-through stabilization wire for applying tension during stenting of the left and right carotid arteries.

In one embodiment, a sheath catheter is percutaneously inserted at the groin and directed through the descending aorta to the aortic arch. A snare is inserted through the sheath and linked with a 0.014 inch or 0.018 inch guide wire from the right subclavian artery (via the right radial or brachial artery access) to provide a stabilization wire for the operational catheter. At this stage, the stabilization wire and the main guide wire occupy the sheath catheter. A reverse curve catheter is then inserted through the sheath catheter over the main guide wire, parallel to the stabilization wire and guided to the common carotid artery from the aortic arch. A stiff guide wire is then inserted through the reverse catheter to the location of the procedure. The reverse curve catheter is then removed leaving the guide wire in the location of the procedure. The bifurcated catheter is then guided to the aortic arch with one stabilization leg over the stabilization wire and the other operational leg over the stiff guide wire such that the operational leg is guided into the common carotid artery while the stabilization leg is guided over the stabilization wire into the subclavian artery. The stiff guide wire is then removed leaving the operational leg of the bifurcated catheter in place for treatment procedures.

In one embodiment, a secondary stabilization wire having a small diameter, e.g., 0.014 or 0.016 inch, is guided through a, for example, Fr-3 or Fr-5, micro sheath, which is placed percutaneously through the right radial or brachial artery and threaded through the subclavian artery and snared into the main guide catheter to stabilize the distal tip. This way, the tension can be applied to the distal tip of the guide catheter to stabilize it in a more planar orientation by putting tension on the stabilization wire, as discussed above, to aid in the stabilization of the guide catheter, which is placed under fluoroscopy (C Arm) in the aorta using percutaneous access. This secondary stabilization wire is hence inserted into the right radial or brachial artery and guided through the right subclavian artery and down and out of the guide catheter. Though the description is provided for the secondary access via the right radial of brachial artery, it should not be considered limiting. It is possible to provide the secondary access via the left radial or brachial artery, external carotid artery or common carotid artery (instead of just the right radial or brachial artery). It may also be possible to have more than one accessory access to complete the procedure using the device. Once the stabilization wire is established, a tension is applied to one or both ends of the secondary stabilization wire to help stabilize the distal end of the guide catheter during the accessing of the left or right internal carotid artery. This allows the stent delivery system to track more easily through the acute anatomy of the arch, especially one such as a type III arch.

In another embodiment, the bifurcated catheter is preloaded into the end of the main guide catheter or long sheath. In this embodiment, the bifurcated catheter has a procedural lumen and a second lumen that can accommodate a snare catheter and wire. It will be appreciated, however, that a potential disadvantage of this device is that the catheter will need to be a bigger device to accommodate the two lumens, but the advantage is that it separates the wires from the beginning so that the wires do not inadvertently wrap around each other during the procedure and cause problems. In this embodiment, the guide catheter is provided with a bifurcated distal configuration having two legs in the form of a Y at the distal end. One leg is of a large diameter, typically having an inner diameter or "working lumen" sufficient to allow the passage of a stent delivery system or other therapeutic devices. The second leg is of a smaller diameter than the first leg with an inner diameter sufficient to accept a snare wire and snare the stabilization guide wire. This bifurcated catheter is sized so as to fit easily through the main guide catheter placed at the start of the procedure and is of sufficient length so as to allow the main leg of the bifurcated catheter to be placed into the carotid artery for stenting and other procedures there and above the neck. The secondary leg is of sufficient length so as to be placed over a stabilization wire from the right subclavian artery and cover it sufficiently to prevent damage to the vessels it passes through while providing the necessary stabilization to the main guide catheter and the bifurcated catheter, during procedural manipulations. Both legs of the bifurcated catheter need not be of the same stiffness or durometer to be able to navigate their respective vessels. For instances the main carotid leg may be of a lesser durometer so as to navigate the arch into the selected carotid artery without affecting the natural anatomic configuration whereas the small leg may be stiffer so as to help with the stabilization of the main guide catheter.

In one embodiment, another practical device and method for safely accessing the carotid artery is disclosed. In this a first reverse curve catheter is inserted percutaneously and directed into the right or left common carotid artery (RCCA or LCCA). A secondary wire is inserted in the reverse curve catheter and out of a hole in the catheter at the location of the arch to be captured by a snare wire that is extended out of a protective sheath extended through the subclavian artery (typically via right radial artery access). Once the snare has captured the stabilization wire a more rigid guide wire is extended through the reverse catheter into the common carotid artery towards the location of the procedure. The reverse catheter is then removed leaving both the rigid guide wire and the stabilization wire in place. A sheath/procedural catheter with a conical atraumatic tip and also having therein a second chamber with a hole close to the distal end for providing an exit for the stabilization wire is advanced over the guide wire and stabilization wires to the aortic arch and the sheath catheter is extended on to the location of procedure. Tension is applied to the stabilization wire for providing support to any working catheter that is inserted through the sheath catheter after removal of the stiff guide wire for conducting the procedure as needed.

In some embodiments, a sheath cover may be used for the stabilization wire as it extends into the subclavian artery when tension is applied prevent unwanted damage to the artery. The stabilized main sheath helps the procedure to be completed and the operational catheter and the sheath catheter to be removed safely.

In some embodiments, a reverse curve guide catheter with a lumen large enough for stenting is used to select the common carotid artery. A secondary wire is inserted in the reverse curve catheter through a parallel lumen in the reverse curve catheter and out of a hole in the catheter at the location of the arch. This secondary wire is then captured by a snare wire with a loop that is extended out of a protective sheath extended through the subclavian artery, typically inserted via right radial artery access. The carotid stenting procedure can now proceed in the standard way described above since the reverse curve guiding catheter itself is stabilized and is usable for procedure.

In percutaneous procedures of the vessels originating from a tortuous aortic arch, the use of stabilization wires in addition to guide wires to guide and stabilize the delivery catheters used to access the left or right carotid arteries is disclosed. The need for the stabilization of the sheath, the embolic protection device (EPD) and the stent delivery system (SDS) is to prevent the uncontrolled prolapse of the sheath, EPD and SDD during stenting procedure in the ascending aorta. This type of prolapse can result in cerebral embolism or stroke in patients by the dragging of the fully deployed EPD across critical carotid internal artery stenosis. Embodiments of the invention provide for stabilizing the sheath, the EPD and the SDS within the left or right carotid arteries by providing a secondary stabilization wire that holds the primary sheath in place within the tortuous aortic arch during the procedure, thereby providing the necessary stability for the SDS within the carotid artery during the procedure. These stabilizing wires typically originate from a low profile radial or brachial artery access and provide a through-and-through tension and support to the sheath by enabling the application of tension to one or either end of the stabilization wire through a typical micro-sheath or catheter. In this embodiment the brachial artery or a small radial artery is usable with the micro-sheath, and similarly in the case of another embodiment described the sheath catheter is used to puncture the radial artery or the brachial artery for entry, to provide adequate hemostasis while keeping the entry profile low. In one embodiment, the stabilization wire has a small diameter, e.g., 0.014 or 0.018 inch diameter, the micro-sheath has a 3 Fr. Diameter, and the sheath catheter has a 5 Fr. Diameter. The use of the small size wire and micro-sheath is useful in preventing hematoma in the brachial artery, which can be devastating in patients receiving anticoagulation drugs, such as Heparin, and anti-platelet therapy such as Plavix, during or after the procedure. The stabilizing wire from the brachial artery enters the aortic arch through the right subclavian artery to be captured and brought out through the sheath at its proximal end. Due to their diameter and forces applied during the procedures, the guide wires, if used without proper covering can inadvertently cause trauma to the associated tortuous vessels walls. The bifurcated catheter disclosed herein provides the necessary protection to the arch and the subclavian artery while providing the necessary stabilization to the sheath, SDS and EPD for access and procedures within the carotid arteries, especially for above the neck procedures. The bifurcated catheter disclosed includes a main catheter that divides into two separate catheters forming a "Y" shape. One leg of the catheter has a smaller diameter with a smaller working lumen (inner diameter), to carry the stabilizing wire, than the second leg of the catheter that has a larger working lumen for arterial stenting operations. This device provides the necessary stability to the system for stenting of the carotid arteries while addressing the percutaneous intervention related trauma to the vessels associated with type-III hostile aortic arches that arise therefrom. Multiple embodiments of the invention are described here under. Even though in the examples described the secondary access is shown as being established via the right radial or brachial artery, it should not be considered limiting in any way. The secondary access may be established via any of the left radial or brachial artery, external carotid artery or common carotid artery (instead of just the right radial or brachial artery). It may also be possible to have more than one accessory access to complete the procedure using the device.

A first embodiment of the invention is described with reference to the schematic diagrams shown in FIGS. 2 to 7 and the flow chart of FIG. 8A. This embodiment illustrates the ability to conduct procedures such as stenting in the left internal carotid artery (LICA) 16 using a procedural catheter that can be inserted through the aortic arch 13 and left common carotid artery 15.

Figure 2:
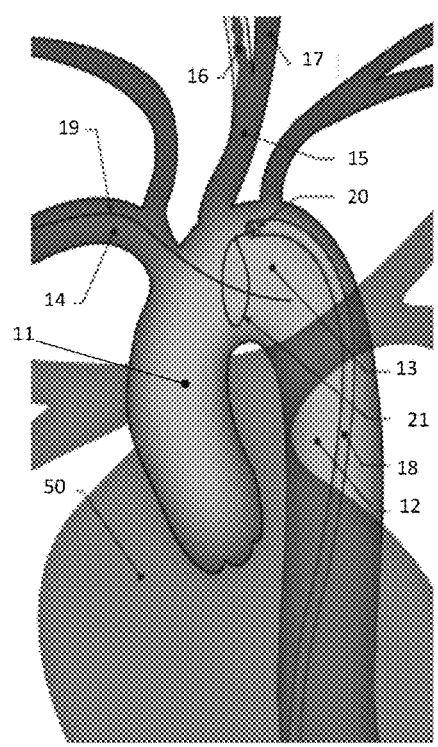
FIG. 2 is a schematic diagram illustrating a distal end of a device with a snare wire extended from the main guide catheter capturing a stabilization wire from the subclavian artery (SA) in accordance with one embodiment of the invention.

As shown in FIG. 2, a sheath catheter 18 is initially inserted percutaneously and guided using fluoroscopic tracking using the opaque metal ring 20 at its distal end. In one embodiment, the sheath catheter 18 is a 7 French (Fr) or 8 Fr sheath; it will be appreciated that differently sized sheath catheters may be used as known to those of skill in the art. The sheath 18 is guided through the femoral artery and the descending thoracic aorta 12 to the aortic arch 13. A snare wire is inserted through the sheath 18 and extended to the aortic arch 13 with a snare loop 21. In one embodiment, the snare loop has a diameter that is any value or range of values between about 20 to 30 mm; it will be appreciated that the diameter may be less than about 20 mm or greater than about 30 mm.

Figure 3:
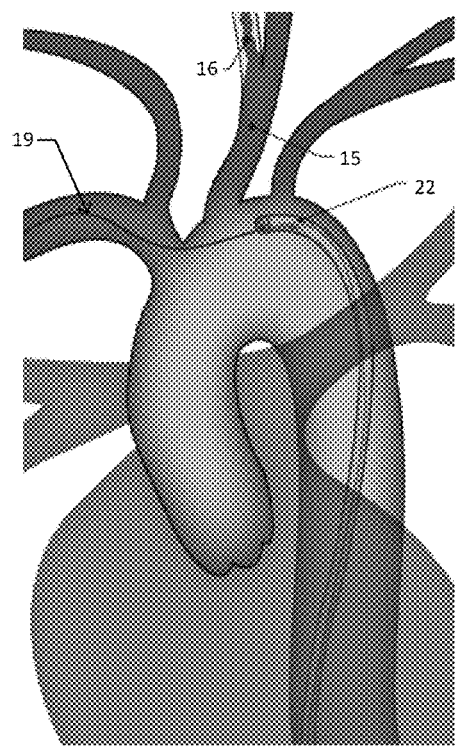
FIG. 3 is a schematic diagram illustrating the aortic arch with a stabilization guide wire snared and pulled into the main guide catheter and out the proximal end in accordance with one embodiment of the invention. The bifurcated catheter may or may not be at this stage located just inside the distal tip of the main guide catheter. The bifurcated catheter in one embodiment may be advanced over the wire after step S808A (FIG. 8A) while in another embodiment the bifurcated catheter may be pre-loaded at the distal tip of the main guide catheter (FIG. 8B).

A second stabilization wire 19 is inserted through the radial artery and guided through the subclavian artery 14 to the aortic arch 13. In one embodiment, the second stabilization wire has about a 0.014 inch diameter. The stabilization wire 19 is captured by the snare 21 and then pulled into the sheath catheter 18, as shown in FIG. 3. In one embodiment, the snare 21 pulls the stabilization wire such that it exits the proximal end of the sheath 18 to form a through-and-through stabilization wire. In one embodiment, a 3 Fr. to 5 Fr. sheath may be used over the 0.014 stabilization wire 19 to reduce slicing and trauma to the arteries the wire is guided through.

Figure 4:
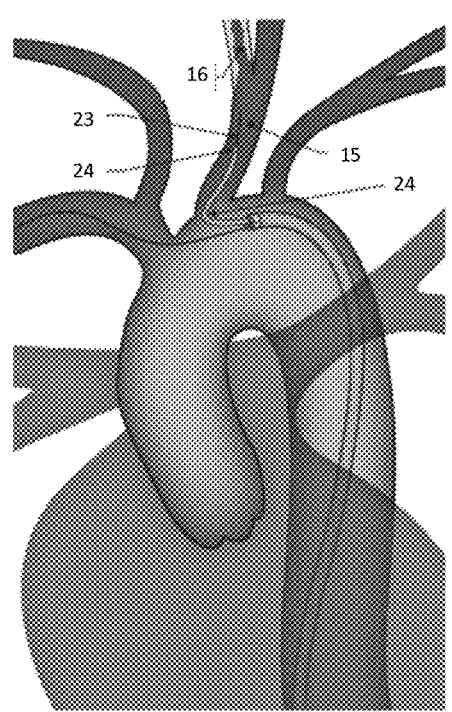
FIG. 4 is a schematic diagram illustrating a reverse curve diagnostic catheter with a guide wire coming out of in the distal tip of the main guide catheter and up into the left common carotid artery in accordance with one embodiment of the invention. In one embodiment, the reverse curve diagnostic catheter with the guide wire is extended out of the sheath or the main guide catheter, and in another embodiment, the bifurcated catheter is at the distal tip of the main guide catheter and the reverse curve diagnostic catheter with the guide wire comes out of the larger leg of the bifurcated catheter.

A reverse curve catheter 24 with an atraumatic tip is then inserted in parallel with the stabilization wire 19 through the sheath catheter 18, as shown in FIG. 4. The reverse curve catheter 24 is used to select the left common carotid artery 15. A stiff wire 23 is then inserted through the reverse curve catheter 24 to the site of the procedure. In one embodiment, the stiff wire has an approximately 0.035 inch diameter.

Figure 5:
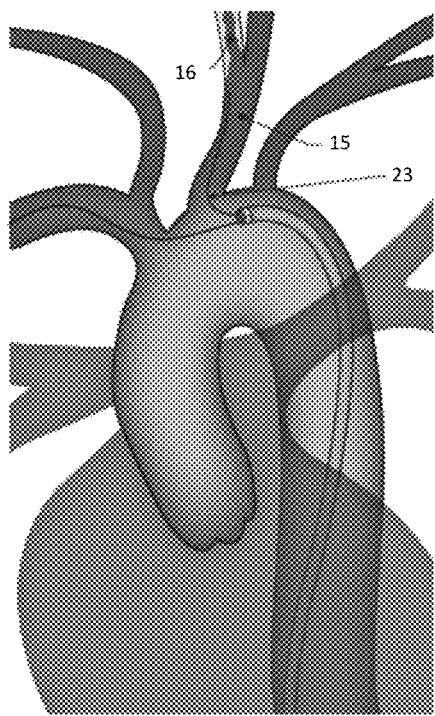
FIG. 5 is a schematic diagram illustrating removal of a reverse curve diagnostic catheter, leaving behind a stiff guide wire in the left common carotid artery in accordance with one embodiment of the invention.

Next, the reverse curve catheter 24 is removed, leaving the stiff wire 23 in the area of the procedure and the stabilization wire 19 in place, as shown in FIG. 5. Both the stiff wire 23 and stabilization wire 19 occupy the large sheath catheter 18, as shown in FIG. 5.

Figure 6:
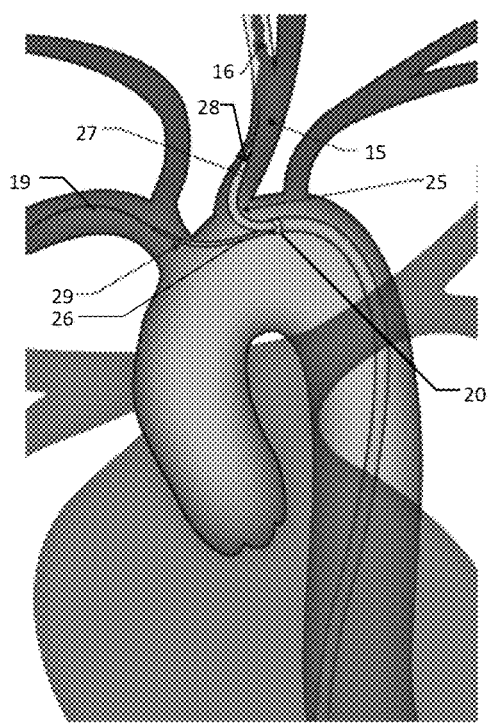
FIG. 6 is a schematic diagram illustrating a bifurcated catheter being advanced out of a main guide catheter over respective guide wires, the large leg over the stiff guide wire into the left common carotid artery and the small leg being advanced over the guide wire into the right subclavian artery in accordance with one embodiment of the invention.

A bifurcated catheter having bifurcations 25 and 26 is then advanced over both the stiff wire 23 and the stabilization wire 19 respectively and out of the guide catheter 18. The large leg (or bifurcation) 25 which contains a procedural catheter tracks along the stiff guide wire 23 into the left common carotid artery 15. The small leg (or bifurcation) 26 tracks along the stabilization wire 19 coming from the right subclavian/innominate artery. Both legs 25, 26 have atraumatic tips 28 to reduce trauma, as shown in FIG. 6.

FIG. 6A is a cross-sectional view of a portion of the bifurcation catheter within the sheath catheter 18. The bifurcation catheter includes a common catheter portion that bifurcates into two separate bifurcations or legs 25, 26 at junction 30. As shown in FIG. 6A, each of the bifurcations of legs 25, 26 include lumens that extend from a distal end of the bifurcation catheter to a proximal end of the bifurcation catheter. As shown in FIG. 6A, the bifurcated leg 25 is configured to slideably receive the guidewire 23, and the bifurcated leg 26 is configured to slideably receive the stabilization wire 19.

Figure 7:
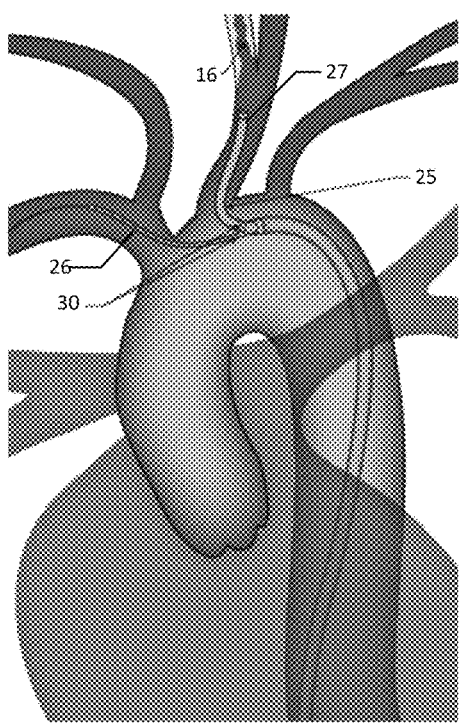
FIG. 7 is a schematic diagram of the legs of the bifurcated catheter advanced out of the main guide catheter and parked into their respective vessels in accordance with one embodiment of the invention. In some embodiments, the atraumatic tips are removed from each leg and the stabilized catheter is ready for procedures.
Figure 6:
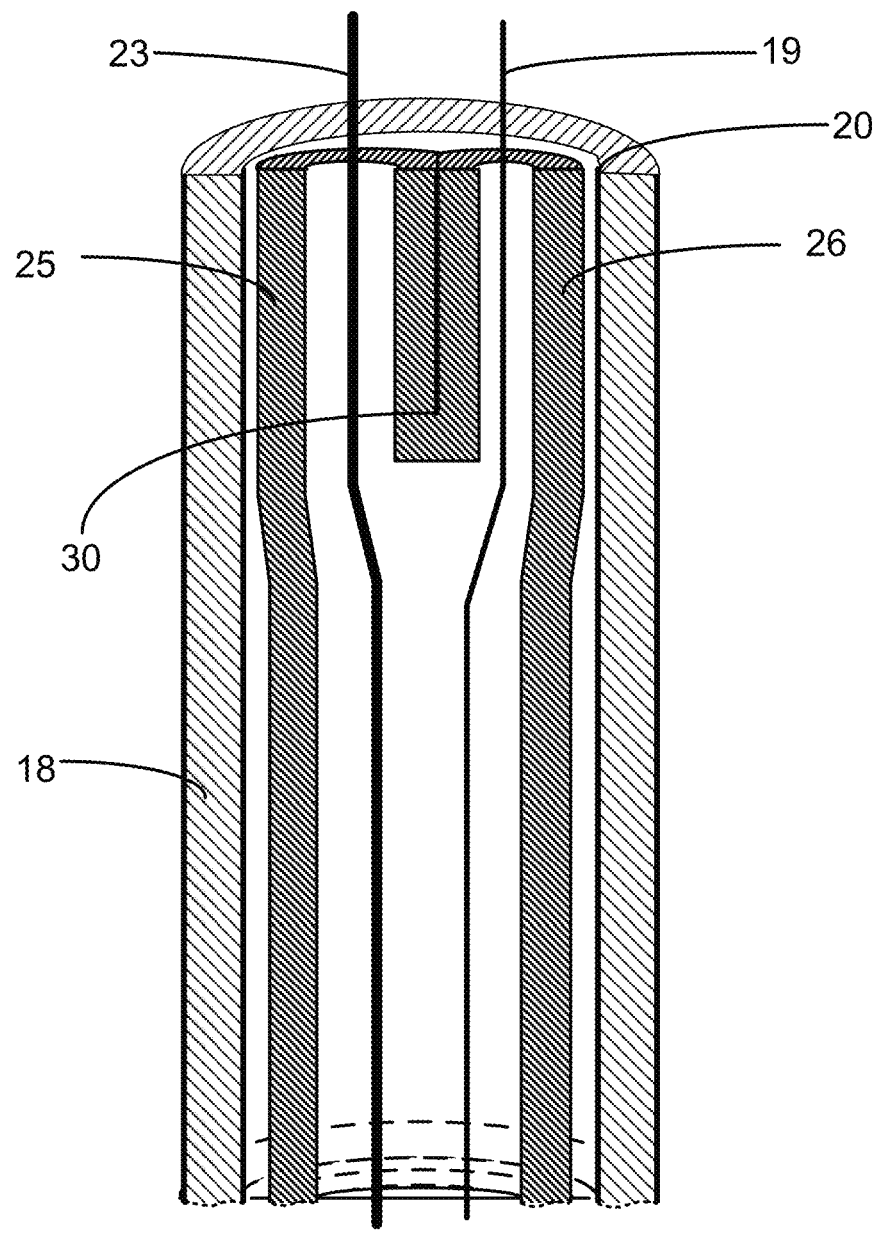

Once the bifurcated catheter is in place, the stiff wire and the atraumatic tips are removed and tension is applied to the stabilization wire from both ends to stabilize and position the operational end of the bifurcated catheter, as shown in FIG. 7.

The bifurcated catheter is now ready for stenting or other procedures in the left internal carotid artery 16.

Figure 8A:
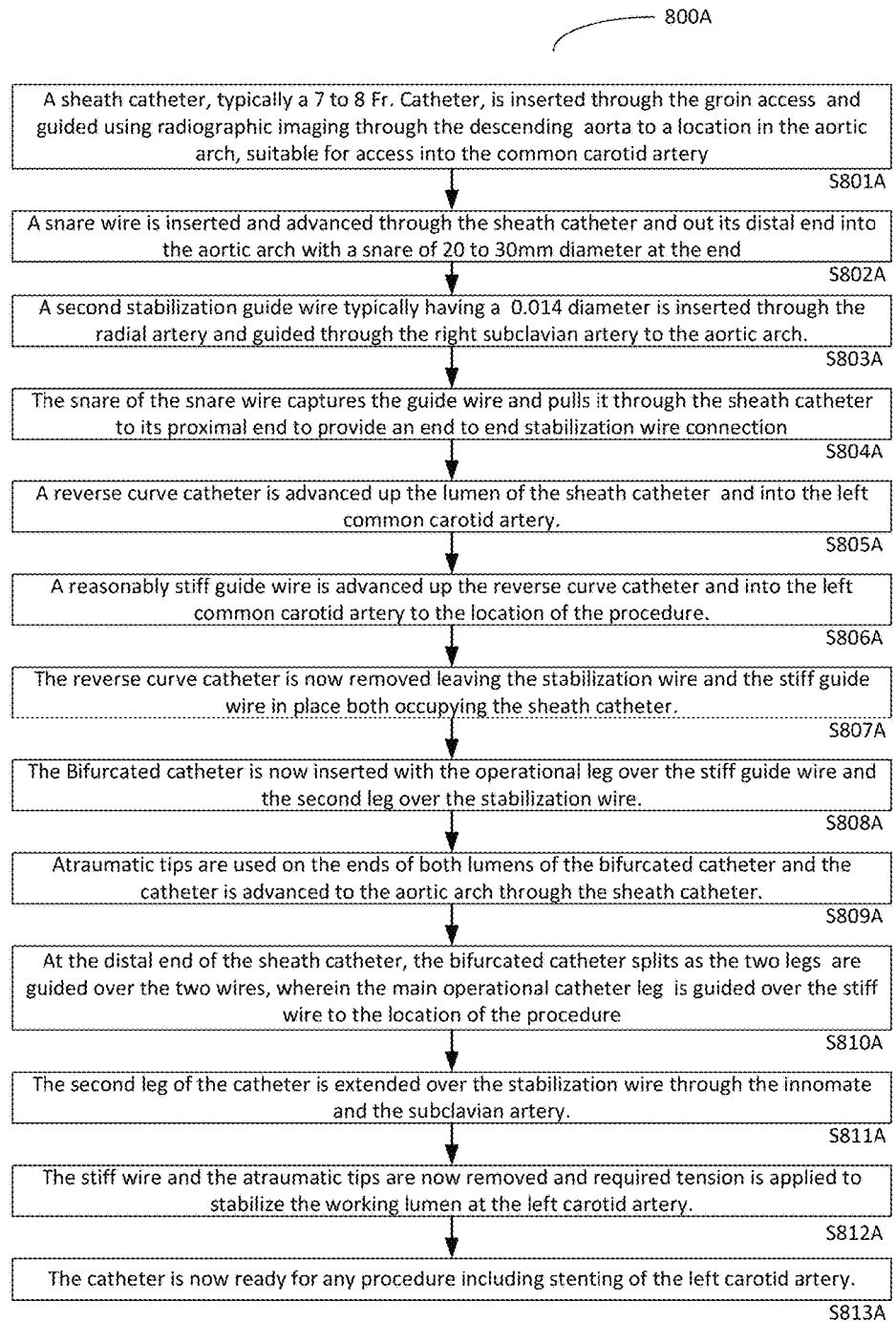
FIG. 8A is a flow chart of a procedure for stabilizing the process catheter and stenting systems in accordance with one embodiment of the invention.
Figure 8:
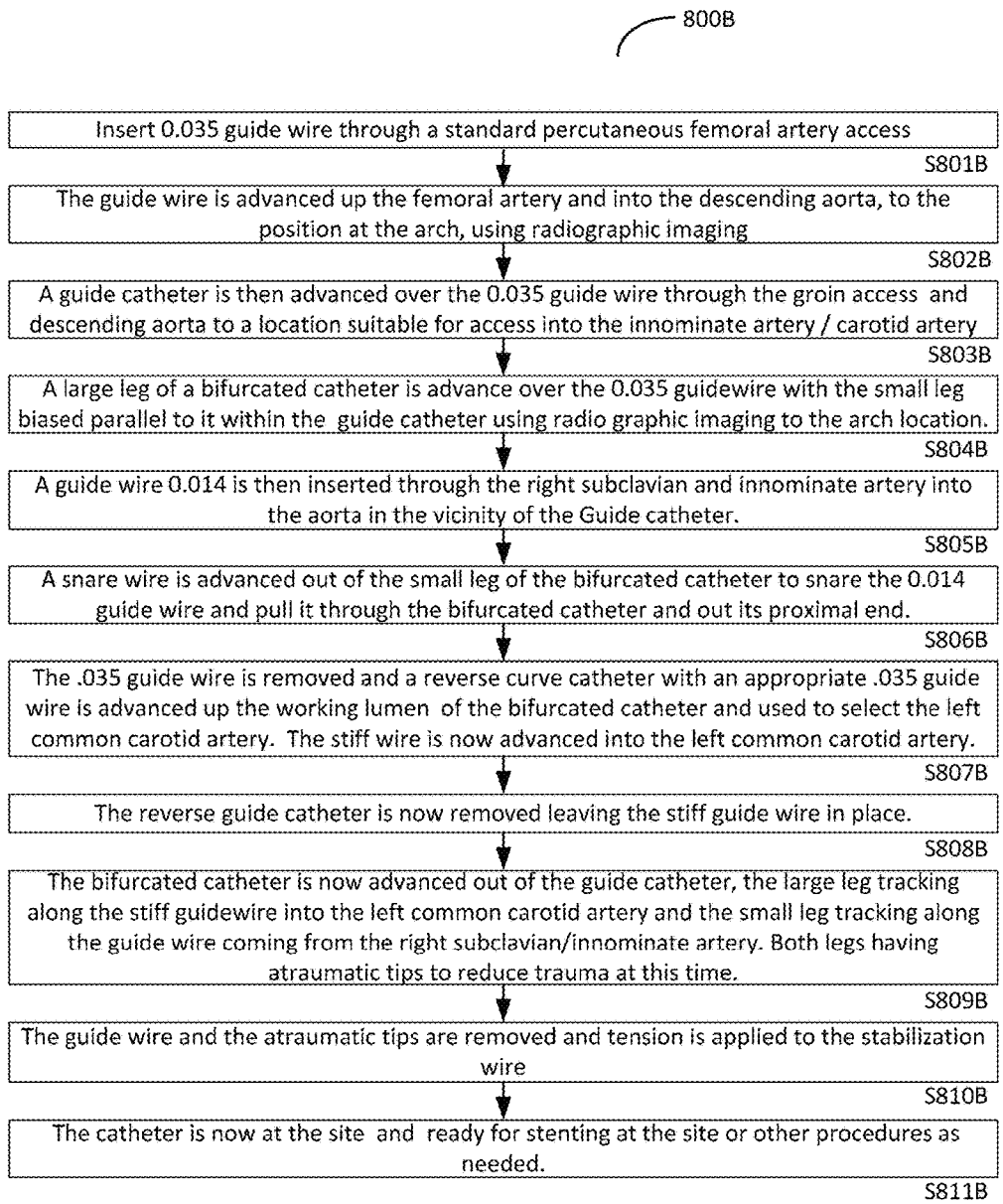
FIG. 8B is a flow chart of a procedure for stabilizing the process and stent catheters in which one of bifurcations of the pre-loaded bifurcated catheter is used to accommodate the snare/stabilization catheter in accordance with one embodiment of the invention.

FIG. 8A illustrates the process 800A described above with reference to FIGS. 2-7.

The process 800A begins by inserting a sheath catheter 18 catheter through the groin access and guided using radiographic imaging using the opaque ring 20 at its distal end through the descending aorta 12 to a location in the aortic arch 13 suitable for access into the left common carotid artery 15 (block S801A).

The process 800A continues by inserting and advancing a snare wire through the sheath catheter 18 and out its distal end into the aortic arch 13 (block S802A).

The process 800A continues by inserting a second stabilization guide wire 19 through the radial artery and guiding it through the right subclavian artery 14 to the aortic arch 13 (block S803A).

The process 800A continues by using the snare loop 21 of the snare wire to capture the guide wire 19 and pull it through the sheath catheter 18 to its proximal end to provide an end-to-end stabilization wire over which tensions can be applied (block S804A).

The process 800A continues by advancing a reverse curve catheter 24 up the lumen of the sheath catheter 18 and into the left common carotid artery 15, again using the opaque ring 25 at its distal end (block S805A).

The process 800A continues by advancing a reasonably stiff guide wire 23 up the reverse curve catheter 24 and into the left common carotid artery 15 to the location of the procedure near the left internal carotid artery 16 (block S806A).

The process 800A continues by removing the reverse curve catheter 24, leaving the stabilization wire 19 and the stiff guide wire 23 in place, both occupying the lumen of the sheath catheter 18 (block S807A).

The process 800A continues by inserting a bifurcated catheter having a main operational leg 25 over the stiff guide wire 23 and having a stabilization leg 26 over the stabilization wire 19 (block S808A).

The process 800A continues by advancing the bifurcated catheter having atraumatic tips 28 on the end of the main operational catheter leg 25 to the aortic arch 13 through the sheath catheter 18 (block S809A).

The process 800A continues by advancing the main operational leg 25 to the location of the procedure by advancing the main operational catheter leg 25 over the stiff wire 23 (block S810A).

The process 800A continues by extending the second leg 26 of the bifurcated catheter over the stabilization wire 19 through the innominate and the subclavian artery 14 (block S811A).

The process 800A continues by removing the stiff wire 23 and the atraumatic tips 28 and applying tension to the stabilization wire 19 to stabilize the working lumen leg 25 at just below the left internal carotid artery 16 (block S812A).

The process continues by performing any treatment procedure, including stenting of the left internal carotid artery 16, through the main operational catheter leg 25 (block S813A).

In another embodiment, the bifurcated catheter accommodates the snare catheter in the secondary lumen. In this embodiment, one leg 25 of the bifurcated catheter is used as the procedural catheter and the other leg of the bifurcated catheter 26 is used initially to send in the snare loop 21 and capture the stabilization wire 19. A reverse curve catheter 24 is sent through the procedural leg 25 of the bifurcated catheter into the LCCA 15 or RCCA and the stiff guide wire 23 is placed at the location of the procedure site. The second leg of the bifurcated catheter already at the aortic arch 13 is equipped with an atraumatic tip 28 and guided along the wire 23 to the location of the procedure. At the same time, the first leg 26 of the bifurcated catheter is extended to cover the stabilization wire 19 into the subclavian artery 15. The atraumatic tip 28 and the stiff wire 23 are then removed and the second leg 25 of the bifurcated catheter is ready for the next treatment steps at the site, including stenting or other procedures. This embodiment is further described with reference to FIGS. 2-7 and FIG. 8B.

In this embodiment, a bifurcated catheter is inserted with the main sheath catheter. In this embodiment, the bifurcated catheter has two chambers therein, one for the procedure and the second chamber for the snare catheter, snare loop/wire, and stabilization wire. This enables passing a snare catheter, snare loop/wire and stabilization wire all through a second chamber/branch of the bifurcated catheter when it is at the apex of the curve of the aortic arch similar to the process described earlier. The process is described below with reference to FIGS. 2-7 and flow chart 800b of FIG. 8B.

FIG. 2 illustrates the distal end of sheath catheter device 18, showing the distal end 20 of the device percutaneously inserted and advanced through the descending thoracic aorta 12 to the aortic arch 13. The bifurcated catheter (not shown) is inserted with the sheath catheter and advanced to the aortic arch 13. A snare wire with a 20 to 30 mm snare is shown extended from the sheath catheter in FIG. 2. In this embodiment, the snare is within the smaller chamber of the bifurcated catheter within the sheath catheter. The snare captures a stabilization wire 19 that is extended into the aortic arch 13 from the right subclavian artery (RSA) 14, as shown in FIG. 2. FIG. 2 further shows the ascending aorta 11, the LCCA 15, the left internal carotid artery 16 and the heart 50.

FIG. 3 shows the snare being tightened 22. In this embodiment, the snared stabilization wire 19 is pulled into the smaller lumen of the bifurcated catheter (not shown) and to the proximal end of the same to provide and end-to-end stabilization for the procedural catheter.

FIG. 4 shows a reverse curve catheter 24 such as a Simmons catheter with a stiff wire 23 being extended from the sheath catheter 18. The reverse curve catheter 24 is extended through the second, larger chamber of the bifurcated catheter into the CCA 15 and advanced to the site of the procedure at just below the left internal carotid artery 16.

The left carotid artery is shown in the figures but it is not meant to be limiting as procedures in both right and left carotid can be addressed with this implementation. Also the carotid artery may be selected with the same reverse guide catheter and a softer guidewire. Once selection has occurred the softer guidewire may be exchanged for the stiffer guidewire.

FIG. 5 shows the stiff wire/guide wire 23 being left at the intended site of the procedure after removal of the reverse catheter.

FIG. 6 shows the bifurcated catheter being advanced with the large lumen 25 over the stiff wire 23 to the site of the procedure and the small lumen 26 over the stabilization wire 19. An atraumatic tip is used to reduce trauma to the artery during this catheter advance.

FIG. 7 shows the catheter 25 with the wire and the atraumatic tips removed and ready for the procedure. Stabilization for the process catheter is provided by applying tension to the stabilization wire 19, to stabilize and fix the location of the sheath catheter and the position of the bifurcation.

FIG. 8B illustrates a process 800B for stabilizing and fixing the location of the sheath catheter and the position of the bifurcation catheter in accordance with one embodiment of the invention.

The process 800B begins by inserting a guide wire 23 through the femoral artery percutaneously (block S801B).

The process 800B continues by advancing the guide wire 23 through the descending thoracic aorta 12 to the aortic arch 13 using radiographic imaging (block S802B).

The process 800B continues by inserting a guide or sheath catheter 18 having a platinum ring 20 that is opaque to X-ray at its distal end through the groin access and guiding the sheath catheter 18 through the descending aorta over the guide wire to the aortic arch 13 to a location suitable for access into the left common carotid artery 15 and the left internal carotid artery 16 that is being accessed for the procedure using x-ray fluoroscopy (block S803B).

The process 800B continues by inserting the larger leg of the bifurcated catheter 25 with the smaller leg 26 arranged parallel to it and guiding the bifurcated catheter over the guide wire 23 to the distal edge 20 of the sheath catheter 18 (block S804B).

The process 800B continues by inserting a stabilization guide wire 19 through the brachial artery preferably using a micro sheath and advancing the stabilization guide wire 19 through the right subclavian artery 14 into the aortic arch 13 (block S805B).

The process 800B continues by extending a second segment of the stabilization guide wire having a snare 21 at its distal end out of the smaller leg 26 of the bifurcated catheter to capture the stabilization wire 19 from the subclavian artery and pull it through the smaller leg of the bifurcated catheter and out to its proximal end providing an end to end stabilization wire for stabilizing the sheath and the bifurcated catheter (block S806B).

The process 800B continues by advancing a reverse guide catheter 24 through the tortuous connection of the left common carotid artery 15 to the aorta at the aortic arch 13 over a reasonably stiff wire 23 up the working lumen of the larger leg of the bifurcated catheter through the left common carotid artery 15 just below the left internal carotid artery 16 where the procedure is to be carried out (block S807B).

The process 800B continues by removing the reverse guide catheter 24 and leaving the stiff guide wire 23 in place as a guide to the bifurcated catheter (block S808).

The process 800B continues by advancing the bifurcated catheter out of the guide catheter, the large leg 25 of the bifurcated catheter tracking along the stiff guide wire 23 into the left common carotid artery 15 and the small leg 26 tracking along the guide wire 19 coming from the right subclavian/innominate artery (block S809).

The process 800B continues by removing the guide wire 23 and the atraumatic tips 28 and applying tension to the stabilization wire 19 to stabilize the main catheter leg 25 extending to just below the left internal carotid artery 16 (block S810).

The process 800B continues by performing a treatment procedure, such as stenting or other procedures as needed, at the treatment site (block S811).

FIGS. 9 to 15 and FIG. 16 illustrate another embodiment of the invention in which a modified snare bifurcated sheath with a side hole is used instead of the bifurcated catheter to provide stability to the procedural catheter used for stenting and other procedures in the carotid arteries. In this embodiment, the snare loop is inserted through the subclavian artery to capture the snare wire and provide a through-and-through capability for stabilization of the procedural catheter. In some embodiments, the snare loop is inserted through the subclavian artery via a right radial or brachial artery access.

Figures 9, 10:
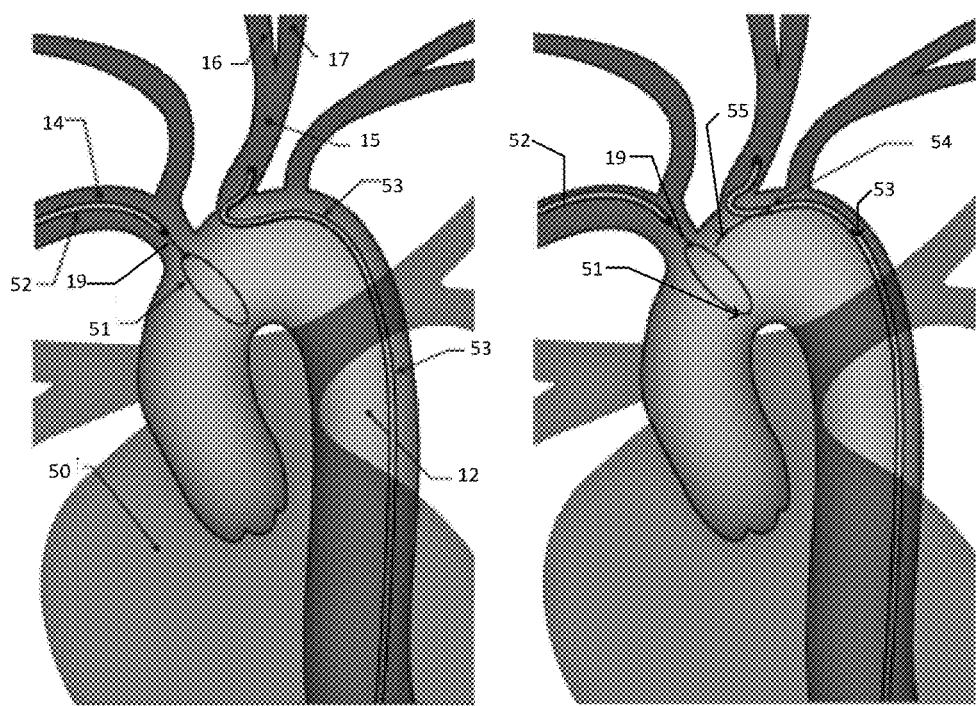
FIG. 9 is a schematic diagram showing the snare wire extended from a protective sheath through the subclavian artery (AS) in accordance with one embodiment of the invention.
FIG. 10 is a schematic diagram showing a wire extended out of a side hole of the initial reverse curve diagnostic catheter to be captured by the snare in accordance with one embodiment of the invention.

FIG. 9 shows a snare wire 19 having a snare loop at its distal end inserted through the radial artery using a sheath 52 extended through the right subclavian artery 14 into the aortic arch 13. In one embodiment, the sheath 52 is a Fr 5 sheath. In one embodiment, the snare loop 51 has a 30 to 40 mm diameter. A reverse curve catheter 53, such as a Simmons catheter, is inserted through the groin access and guided through the descending aorta 12 to select the left common carotid artery 15 (it can also be used to select the right carotid artery). In one embodiment, the reverse curve catheter 53 is a Fr. 5 catheter.

FIG. 10 further shows a secondary stabilization wire 55 that is inserted from the proximal end of the reverse curve catheter 53 and exited out of a hole 54 on the side of the catheter 53 at the location at the apex of the curve of the aortic arch 13. In one embodiment, the secondary stabilization wire has a 0.014 diameter.

Figure 11:
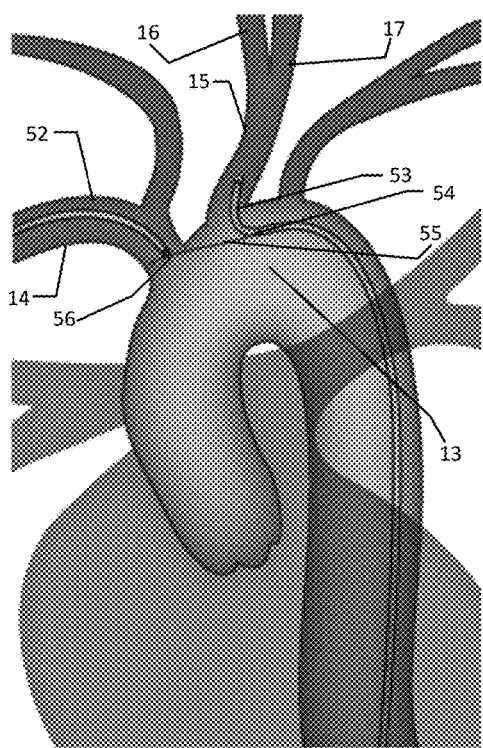
FIG. 11 is a schematic diagram illustrating capturing the stabilization wire by the snare wire loop in accordance with one embodiment of the invention.

FIG. 11 shows the stabilization wire 55 being snared by the snare 56 to provide a tensionable stabilization capability comprising the snare 56 from the sheath catheter 52 coming from the right subclavian artery and the snared wire 55 coming from the reverse curve catheter 53.

Figure 12:
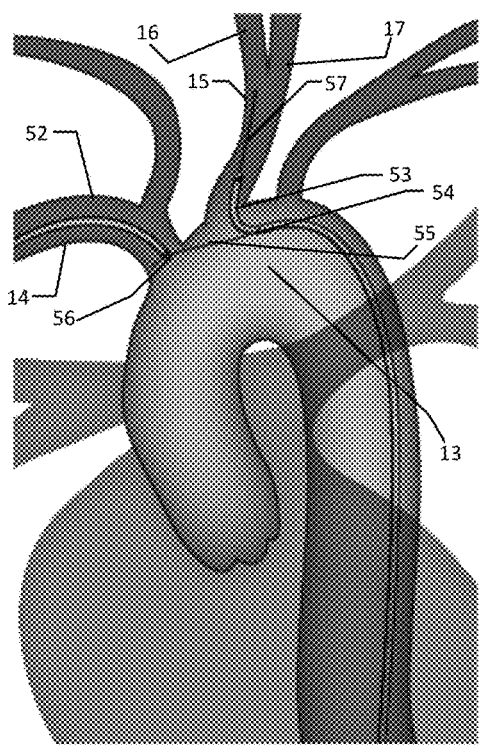
FIG. 12 is a schematic diagram of the extension of a stiff guide wire from the reverse curve Simmons catheter into the carotid artery in accordance with one embodiment of the invention.

FIG. 12 further shows a stiff guide wire 57 being extended from the reverse catheter 53 into the left common carotid artery 15 and below the left internal carotid artery 16 where the procedure is expected to be carried out once the tensionable stabilization is established.

FIG. 13 shows the withdrawal of the reverse catheter 53 leaving both the snare 56, snared stabilization wire 55, and the stiff guide wire 57 into the left common carotid artery 15, and below the left internal carotid artery 16.

FIG. 14 shows a bifurcated sheath catheter 58 having two chambers—one for the stabilization wire and the other for the process catheter with an atraumatic dilator tip 59, being guided over the stiff guide wire and the stabilization wire 55, which exits the sheath through a hole 60, in the sheath catheter 58. In one embodiment, the bifurcated sheath catheter 58 is a Fr.6 or Fr.7 sized catheter.

Figure 15:
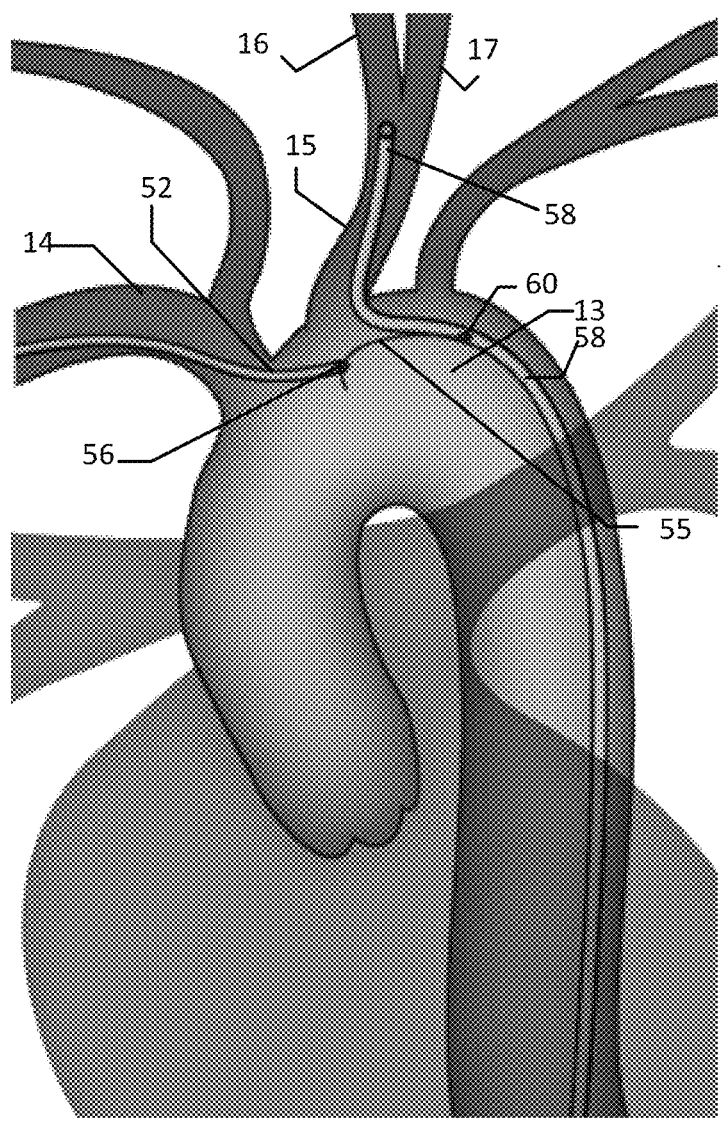
FIG. 15 is a schematic diagram of the working sheath catheter advanced to the location of the procedure and the guide wire removed in readiness for a procedure in accordance with one embodiment of the invention.

FIG. 15 shows the sheath catheter 58 with the stiff wire and atraumatic tip removed with the snared stabilization wire 55, forming an end-to-end wire enabling stabilization tension to be applied to stabilize the sheath catheter 58 extending into the left internal carotid artery 16 for inserting the procedural catheter for stenting and other procedures from the aortic arch 13.

In yet another embodiment, the initial sheath catheter may have two lumens, one for the support and stabilization wire and a second as the operational catheter. Further, the operational catheter may be made with a softer operational leg at its distal end which can be used as a reverse curve guiding catheter as well. By combining the application capabilities of such a catheter, it is possible to reduce the number of catheters used and hence the number of steps needed for set up and completion of the procedure.

Figure 16:
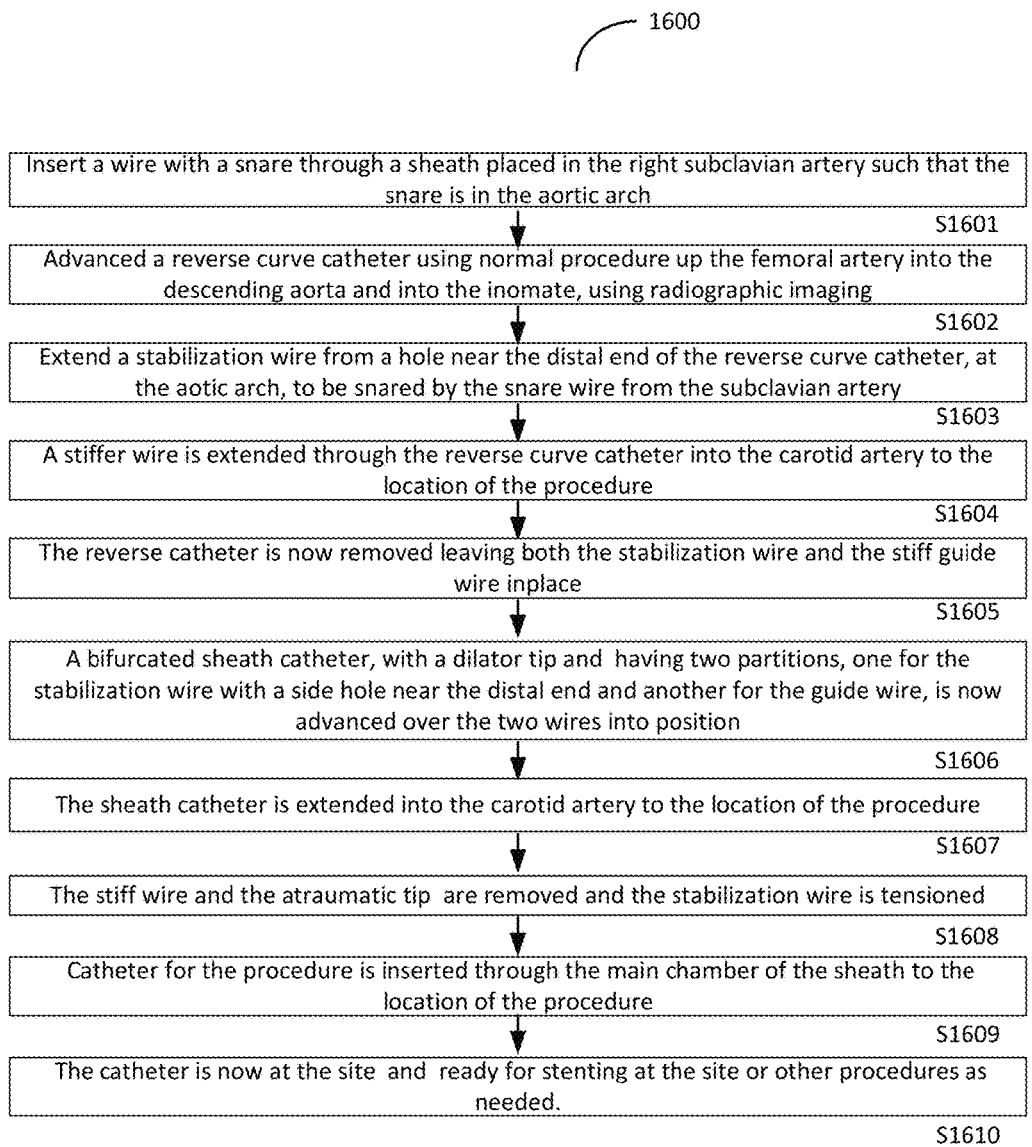
FIG. 16 is a flow diagram for stabilizing the process catheters and systems in accordance with one embodiment of the invention.

FIG. 16 is flow chart illustrating a process 1600 according to another embodiment of the invention.

The process 1600 begins by inserting a wire with a snare 51 through a sheath 52 that is inserted through the radial artery and directed through the right subclavian artery 14 such that the snare is in the aortic arch 13 (block S1601).

The process 1600 continues by percutaneously inserting and advancing a reverse curve catheter 53 up the femoral artery into the descending thoracic aorta 12 into the left common carotid artery 15 using radiographic imaging (block S1602).

The process 1600 continues by inserting a secondary stabilization wire 55 into the reverse curve catheter 53 at the proximal end and exited from a hole 56 near the distal end of the reverse curve catheter at the aortic arch 13 to be snared by the snare 51 from the subclavian artery 14 (block S1603).

The process 1600 continues by snaring the stabilization wire 55 to provide an end to end stabilization (55) to the catheter, and extending a stiff guide wire 57 through the reverse curve catheter 53 into the left common carotid artery 15 to the location of the procedure (block S1604).

The process 1600 continues by removing the reverse curve catheter 53, leaving both the stabilization wire 55 and the stiff guide wire 57 in place in the arteries (block S1605).

The process 1600 continues by advancing a bifurcated sheath catheter 58 having two partitions (one for the stabilization wire 55 with a side hole 60 near the distal end and another with a dilator tip 59 for the guide wire 57) over the two wires into position such that the sheath catheter for process 58 is extended into the carotid artery 16 while the stabilization wire 55 through the hole 60 in the bifurcated sheath catheter 58 extends from the proximal end of the sheath catheter 58 through the hole 60, through the aortic arch 13 and subclavian artery 14 to provide a through and through capability to provide tension and stabilization to the operating catheter 58 (block S1606).

The process 1600 continues by extending the sheath catheter into the left internal carotid artery 16 to the location of the procedure (block S1607).

The process 1600 continues by removing the stiff guide wire 57 and the atraumatic dilator tip 58 and tensioning the stabilization wire 55 to provide stability to the sheath catheter 58 (block S1608).

The process 1600 continues by inserting the catheter for the procedure through the main chamber of the sheath 58 to the location of the procedure in the left internal carotid artery 16 (block S1609).

The process 1600 continues by performing a stenting or other procedure at the treatment site (block S1610).

In another embodiment, a reverse curve catheter with a lumen sufficiently large for stenting instead of a sheath catheter may be used. In this embodiment, the reverse curve catheter having two lumens, one large procedural lumen and the other a smaller stabilization lumen, is used to select the carotid artery. A secondary wire is inserted in the reverse curve catheter (through the stabilization lumen) and out of a hole in the reverse curve catheter at the location of the arch. This secondary wire is then captured by a snare wire with a loop that is extended out of a protective sheath extended through the subclavian artery. The carotid stenting procedure can now proceed in the standard way using the procedural lumen of the reverse curve catheter since the reverse curve guiding catheter itself is stabilized and is usable for procedure.

Though the examples provide show specific access points for the procedural catheter and the stabilization wires it is not meant to be limiting. There may be other scenarios possible. For example, in an alternate scenario, the main access is through the right radial artery and the stabilization wire or snare is introduced from the groin access or even the left radial artery access. Also the main access may be from the left radial artery with the stabilization wire or snare still comes out through the right subclavian artery.

As will be understood by those familiar with the art, the invention may be embodied in other specific forms without departing from the spirit or essential characteristics thereof. Likewise, the particular naming and division of the members, features, attributes, and other aspects are not mandatory or significant, and the mechanisms that implement the invention or its features may have different structural construct, names, and divisions. Accordingly, the disclosure of the invention is intended to be illustrative, but not limiting, of the scope of the invention.

While the invention has been described in terms of several embodiments, those of ordinary skill in the art will recognize that the invention is not limited to the embodiments described, but can be practiced with modification and alteration within the spirit and scope of the appended claims. The description is thus to be regarded as illustrative instead of limiting. There are numerous other variations to different aspects of the invention described above, which in the interest of conciseness have not been provided in detail. Accordingly, other embodiments are within the scope of the claims.

The invention has been described in relation to particular examples, which are intended in all respects to be illustrative rather than restrictive. Those skilled in the art will appreciate that many different combinations will be suitable for practicing the present invention. Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. A carotid percutaneous intervention system configured to provide end to end stabilization and support for a procedural catheter using a bifurcated catheter, the system comprising:
   a sheath catheter percutaneously insertable through a femoral artery access and positionable in an aortic arch, the sheath catheter comprising a proximal end and a distal end, wherein the proximal end is located at the femoral artery access;
   a stabilization wire, comprising a proximal end and a distal end, insertable through a percutaneous radial artery access and deliverable to the aortic arch, wherein the stabilization wire is further extendable through the sheath catheter and out of the proximal end of the sheath catheter at the femoral artery access, wherein the proximal end of the stabilization wire is at the percutaneous radial artery access and the distal end of the stabilization wire is at the femoral artery access; and
   wherein the stabilization wire provides end to end stabilization to a procedural lumen of the bifurcated catheter, during access of a carotid artery, through the procedural lumen of the bifurcated catheter, by the procedural catheter and during subsequent procedures within the carotid artery, by application of tension on the stabilization wire between the proximal end at the radial artery access and the distal end at the femoral artery access; wherein a first leg of the bifurcated catheter is deliverable over the guide wire to the treatment site; and a second leg of the bifurcated catheter is positionable over the stabilization wire, wherein the first leg and the second leg join with a common catheter portion at a junction, and wherein the junction is positionable within the aortic arch below an ostium of the carotid artery; wherein a distal tip of the first leg and a distal tip of the second leg comprise atraumatic tips to reduce trauma to the arteries that are accessed, the first leg over the guide wire and the second leg over the stabilization wire.

2. The system of claim 1, further comprising:
   a reverse curve catheter insertable through the sheath catheter parallel to the stabilization wire, wherein the reverse curve catheter is configured to access the carotid artery through the aortic arch and an ostium of the carotid artery to further enable insertion of the guide wire.

3. The system of claim 2, further comprising:
the guide wire insertable through the reverse curve catheter, wherein the guide wire is further configured to access the carotid artery and a treatment site.

4. The system of claim 1, wherein the first leg of the bifurcated catheter is stabilized at the treatment sited by applying end to end tension to the stabilization wire.

5. The system of claim 1, further comprising:
a bifurcated catheter having a proximal end and a distal end, wherein the bifurcated catheter comprises a common catheter portion comprising a lumen at the proximal end and a bifurcation comprising a first leg and a second leg at the distal end, and wherein the first leg comprises a first lumen that is larger than a second lumen in the second leg, wherein the second leg of the bifurcated catheter is pre-loaded into the sheath catheter, wherein the snare wire is passed through the second lumen of the second leg of the bifurcated catheter to snare the stabilization wire and pull it through the second lumen in the second leg; and
a reverse curve catheter insertable through the lumen of the common catheter portion and the first lumen of the first leg of the bifurcated catheter to access the carotid artery, wherein stabilization is provided by the stabilization wire that enable stable access to the ostium of the carotid artery and a site of the procedure.

6. The system of claim 5, wherein the first lumen comprises a procedural lumen and wherein the second lumen comprises a stabilization lumen.

7. The system of claim 6, wherein the procedural lumen extends from the proximal end of the bifurcated catheter to the distal end of the bifurcated catheter through the lumen of the common catheter portion and the first lumen of the first leg, and wherein the stabilization lumen extends from the proximal end of the bifurcated catheter to the distal end of the bifurcated catheter through the lumen of the common catheter portion to the second lumen of the second leg.

8. The system of claim 7, wherein the stabilization lumen is for slideably receiving a stabilization catheter or the stabilization wire.

9. The system of claim 1, further comprising:
the procedural catheter insertable through the proximal end of the bifurcated catheter and extending through the first leg of the bifurcated catheter to access the treatment site.

10. The system of claim 1, wherein end-to-end tension is applicable to the stabilization wire between the proximal end and the distal end to stabilize the first procedural lumen of the bifurcated catheter and improve pushability of the procedural catheter while accessing the carotid artery and the treatment site.

11. A carotid percutaneous intervention system comprising:
a sheath catheter percutaneously insertable through a first percutaneous access and positionable in a location at an ostium of a vessel where a procedure is to be performed;
a first wire having a proximal end and a distal end, the first wire comprising a snare at the distal end, wherein the wire is percutaneously inserted into the sheath catheter through the first percutaneous access and positionable at the ostium of the vessel;
a stabilization wire having a proximal end and a distal end, the stabilization wire insertable through a second percutaneous access and guidable to the ostium of the vessel, the distal end of the stabilization wire captureable by the snare and pullable to the first percutaneous access through the sheath catheter;
a bifurcated catheter having a bifurcation comprising an arm with a reverse curve catheter feature and a hole for the stabilization wire at a distal end of the bifurcated catheter, the bifurcated catheter advanceable through the sheath from the first percutaneous access to the location of the ostium of the vessel where the procedure is to be carried out, the bifurcated catheter advanceable over the stabilization wire through the hole at the distal end of the bifurcated catheter;
when the stabilization wire is configured to be pulled by the snare to the first percutaneous access such that the stabilization wire extends out of the first and second percutaneous accesses, the stabilization wire is configured to provide end to end stabilization and pushability to the reverse curve catheter by application of a tension to the proximal end and distal end of the stabilization wire.

12. The system of claim 11, further comprising a stiff guidewire having a proximal end and a distal end, the stiff guidewire insertable through the reverse curve catheter such that the distal end of the stiff guidewire is positionable at the treatment site.

13. The system of claim 12, wherein the reverse curve catheter feature is removable following delivery of the stiff guidewire in the carotid artery.

14. The system of claim 12, further comprising:
a procedural catheter insertable through the bifurcated catheter over the stiff guidewire into the location of the procedure within the vessel through the ostium of the vessel.

15. The system of claim 14, wherein the bifurcation catheter comprises:
a common catheter portion at a proximal end of the bifurcation catheter, the common catheter portion comprising a lumen;
a first leg at a distal end of the bifurcation catheter and comprising a first lumen, wherein the first leg is deliverable over the stiff guidewire to a treatment site; and
a second leg at a distal end of the bifurcation catheter and comprising a second lumen, wherein the second lumen is smaller than the first lumen, and wherein the second leg is positionable over the stabilization wire,
wherein the first leg and the second leg join with the common catheter portion at a junction, and wherein the junction is positionable at the location at the ostium of the vessel where the procedure is to be carried out.

16. The system of claim 15, wherein the junction is Y-shaped.

17. The system of claim 15, wherein the first lumen comprises a procedural lumen and the second lumen comprises a stabilization lumen.

18. The system of claim 17, further comprising:
a procedural catheter insertable through the procedural lumen of the bifurcated catheter after removal of the stiff guidewire.

19. The system of claim 11, wherein the hole comprises a second lumen.

20. A bifurcated catheter for use in a percutaneous intervention system comprising:
a body comprising a proximal end and a distal end, wherein the body comprises:
a common catheter portion at the proximal end, the common catheter portion comprising a lumen;

a bifurcation having a first leg and a second leg at the distal end;

the first leg at the distal end, the first leg comprising a first lumen; and the second leg at a distal end, the second leg comprising a second lumen, the first lumen being larger than the second lumen, the first lumen being of a size to carry a procedural catheter and the second lumen being of a size to only carry a stabilization wire;

wherein the first leg and the second leg join with the common catheter portion at a junction; and wherein the first leg of the bifurcated catheter is configured to be stabilized by application of a tension to the stabilization wire between a proximal end of the stabilization wire at a first percutaneous access and a distal end at a second percutaneous access of the stabilization wire when the stabilization wire is inserted in the second lumen; wherein the body comprises a procedural lumen and a stabilization lumen that extend from the proximal end to the distal end of the body, the procedural lumen of the body comprising the first lumen and the stabilization lumen of the body comprising the second lumen; wherein the procedural lumen extends from the proximal end through the common catheter to the distal end through the first leg, and wherein the stabilization lumen extends from the proximal end through the common catheter to the distal end through the second leg.

21. The system bifurcated catheter of claim 20, wherein the junction is Y-shaped.

22. The bifurcated catheter of claim 20, wherein the stabilization lumen is configured to provide stabilization and pushability to the procedural catheter through the first lumen of the bifurcated catheter.

23. The bifurcated catheter of claim 20, wherein a distal tip of the first leg and a distal tip of the second leg comprise atraumatic tips.

24. The bifurcated catheter of claim 20, wherein the bifurcated catheter is configured to provide stability and pushability to the procedural catheter and stabilization wire, by applying tension on the stabilization wire, thereby protecting the arterial system including the artery, an ostium of the vessel and the vessel itself during manipulation of a guide wire and procedural catheter or procedural equipment.

* * * * *